United States Patent [19]

Webster

[11] Patent Number: 4,664,662

[45] Date of Patent: May 12, 1987

[54] WOUND DRESSING

[75] Inventor: David F. Webster, Bishops Stortford, United Kingdom

[73] Assignee: Smith and Nephew Associated Companies plc, England

[21] Appl. No.: 760,827

[22] Filed: Jul. 31, 1985

[30] Foreign Application Priority Data

Aug. 2, 1984 [GB] United Kingdom ................. 8419745

[51] Int. Cl.$^4$ ............................................. A61F 13/16
[52] U.S. Cl. ..................................... 604/369; 128/156
[58] Field of Search ............... 604/369, 368, 367, 904, 604/370, 358; 128/155, 156

[56] References Cited

U.S. PATENT DOCUMENTS

| 3,812,856 | 5/1974 | Duncan et al. | 604/369 X |
| 3,815,601 | 6/1974 | Schaefer | 604/369 X |
| 3,994,298 | 11/1976 | Des Marais | 604/369 |
| 4,108,180 | 8/1978 | Moehrle | 604/369 |
| 4,226,232 | 10/1980 | Spence | 128/156 |
| 4,475,911 | 10/1984 | Gellert | 604/367 |
| 4,519,798 | 5/1985 | Dinius | 604/358 |
| 4,543,098 | 9/1985 | Wolfe et al. | 604/370 |

*Primary Examiner*—John D. Yasko
*Attorney, Agent, or Firm*—Jacobs & Jacobs

[57] ABSTRACT

An absorbent, non-adherent wound dressing suitable for use in deep and cavernous wounds is described. The dressing comprises an absorbent material in the form of individual pieces of a conformable, resilient, absorbent hydrophilic foam retained within a porous bag formed from a perforated polymeric film. In a preferred form the foam is a hydrophilic polyurethane foam and the perforated polymeric film is a contoured net of a thermoplastic elastomeric polymer. A non-woven fabric may be additionally present between the perforated polymeric film and the pieces of foam. The dressings can absorb large volumes of wound exudate without adhering to the wound.

27 Claims, No Drawings

WOUND DRESSING

The present invention is concerned with an absorbent non-adherent wound dressing which is suitable for use on deep cavernous and exuding wounds and comprises an absorbent material contained within a water permeable, porous bag. More particularly the invention is concerned with a dressing in which the absorbent material comprises individual pieces of conformable, flexible, absorbent foam contained within the bag formed from an apertured film. The present invention is also concerned with the preparation and use of such dressings.

Deep and exuding wounds such as decubitus ulcers, pressure sores, venous stasis ulcers, infected wounds, deep and open surgical incisions and burns present the problem of keeping them clean and free from infection. Blood, serum and other matter if allowed to accumulate in the cavities and crevices of these wounds can encourage bacterial growth and can cause the formation of a crust of organic matter both of which eventualities will discourage and delay wound healing.

Many types of dressing have been suggested to cover and to protect cavernous and exuding wounds. Current treatments include the use of ribbon gauze or tulle gras and conventional gauze which is packed into the cavity of the wound. The material of such dressings absorbs wound exudate but often dries out and forms a hard plug which adheres to the wound. This hard plug is both painful when in place and difficult and painful to remove. Removal often causes further trauma to the wound and hence impairs wound healing. One way of improving the treatment of cavernous wounds is to use in place of a gauze dressing a foam dressing in which a composition is placed in a wound cavity and allowed to polymerise and foam in situ whereby the wound cavity is filled with a solid, one-piece absorbent foam. Such dressings achieve some success. However such dressings suffer from the disadvantages that they are expensive and difficult and time consuming to apply. A further disadvantage is that as the wound heals the cavity becomes smaller and the foam cavity filler has to be removed and pared down or trimmed so that it remains a good fit within the cavity. In order to be reused in this way the plug has to be washed and disinfected to avoid infecting the wound on replacement. Alternatively a new plug has to be cast to take account of the smaller cavity. An alternative form of dressing may be used in which fine particles of an absorbent material are placed in the wound cavity and covered with a protective dressing. It is believed that such fine particulate absorbents will aid wicking of the wound exudate into the absorbent mass and that the particles will retain their integrity so that they can be removed by simply washing off the wound without causing any trauma. Unfortunately such dressings tend to have an insufficient absorption capacity for wound exudate, lack stability on the patient and in some cases the exudate fails to wick effectively between the particles. Recently dressings have been developed in which the wound cavity is filled with gel, which in one embodiment is present in a porous bag formed preferably of long fibre, high wet strength paper. Such dressings are described in United Kingdom Application No. 2048292. These dressings whilst being conformable and flexible in the wound cavity can suffer from the disadvantage that wound exudate is not easily absorbed into and through the gel and so can lead to pooling of exudate underneath the dressing.

It has now been found that by using a wound dressing comprising pieces of an absorbent hydrophilic foam in a porous bag, formed from a perforated polymeric film, a wound dressing is obtained which conforms to the contours of the wound, is absorbent and soft, permits passage of exudate into and between the individual pieces of foam and is non-adherent to the healing wound. On absorption of wound exudate the foam swells but keeps its conformability to ensure that the dressing maintains its contact with the contours of the wound filling the wound cavity and so protecting the wound surface and keeping it moist to encourage rapid re-epithelialisation.

Accordingly the present invention provides an absorbent, non-adherent wound dressing suitable for use on deep wounds which dressing comprises an absorbent material contained within a porous bag characterised in that the absorbent material comprises individual pieces of a conformable, resilient, absorbent hydrophilic foam and the bag is formed from an apertured material.

From the above it is clear that the apertured material may be in the form of a perforated polymeric film.

Accordingly therefore the present invention provides an absorbent, non-adherent wound dressing suitable for use in deep wounds which dressing comprises an absorbent material contained within a porous bag characterised in that the absorbent material comprises individual pieces of a conformable, resilient, absorbent hydrophilic foam and the bag is formed from a perforated polymeric film.

When used herein the term hydrophilic foam means any foam which will absorb fluids such as water, blood, wound exudate and other body fluids. Foams which are prepared by polymerising and foaming hydrophilic monomers or by foaming hydrophilic polymers form a preferred group of foams within the general description of hydrophilic foams.

Aptly the hydrophilic foam is present in the form of individual pieces which confers on the dressing of the invention the property of being able to conform to the contours of the wound cavity both on initial application of the dressing and subsequently following absorption of body fluids. It is believed that existing commercially available foams if used as a single piece possess too high a density to possess the required degree of conformability.

Aptly therefore the hydrophilic foam used to form the individual pieces of the absorbent material for use in the dressings of the present invention will be conformable, that is when placed in a wound cavity the foam will allow the dressing to conform to the contours of the wound both when the patient is at rest and when the body of the patient is in movement. Thus the foam should not be stiff or rigid. The foam will be capable of absorbing wound exudate. It is desirable that the foam will swell on absorbing exudate. This results in the dressing being able to adjust to changing wound contours, for example during movement or as healing proceeds and to ensure that the wound cavity remains filled. The hydrophilic nature of the foam results in both the dressing absorbing exudate quickly and in maintaining the wound surface in a moist condition which many authorities aver is the optimal environment for wound healing. The foam should also be soft and compressible making the dressing comfortable to wear. The dressing is also permeable to air and moisture vapour.

Suitably the foam and hence the wound dressing, will have the capacity to absorb several times its own weight of body fluids such as serum, blood or wound exudate. The amount of body fluid required to be absorbed will of course vary from wound to wound but suitably the dressing will absorb at least three times its weight of body fluid and preferably at least four times its weight of body fluid.

Aptly the foam will be a resilient, open cell foam. Suitable open cell hydrophilic foams will have a cell size of 30 µm to 700 µm and preferably a cell size of 50 µm to 500 µm. Such hydrophilic open cell foams will have 20% to 70% and preferably 30% to 60% of the total membrane area of the cells as membrane openings. Such open cell foams permit transport of fluid secreted from the wound and of any cellular debris into and within the foam as well as between individual peices of the foam. It has been found that this provides an advantage over existing gel, particulate or single piece foam cavity wound dressings wherein if the wound secretion is not conducted away from the wound site those dressing materials may cause the secretion to coagulate and form an inpenitrable crust over the wound leading to pooling of further exudate under the crust and delaying wound healing or causing infection.

Apt foams include polyurethane, carboxylated butadiene-styrene rubber, polyacrylate, polyvinylic or cellulosic foams. Polyvinylic foams include polyvinyl acetal foams formed by the reaction of polyvinyl alcohol and an aldehyde, usually formaldehyde or acetaldehyde. Such foams are generally hard until wetted by water. It is envisaged that such foams may be used dry or may be wetted and squeezed 'dry' whereupon they retain sufficient moisture to remain soft and flexible and are packaged in a waterproof package. Suitable foams may be prepared from hydrophilic materials per se or may be treated to render them hydrophilic, for example with surfactants. It is preferred however to use foams which are made of polymer which is itself hydrophilic. Such foams have been found to be less likely to cause the wound exudate to coagulate rapidly. It is also within the scope of the invention that a blend of two or more foams may be used or a combination of a foam with an absorption enhancing material such as, for example, a cellulose material in a form which is capable of being retained within the bag.

Favoured hydrophilic polymer foams are hydrophilic polyurethane foams. One favoured foam is made of crosslinked hydrophilic polyurethane. Particularly favoured foams can be made by reacting a hydrophilic isocyanate-terminated polyether prepolymer with water. Preferred hydrophilic polyurethane foams of this type include those known as Hypol (trade mark) foams. Hypol foams can be made from Hypol hydrophilic prepolymers marketed by W. R. Grace and Co.

A second favoured foam may be formed by foaming, for example by blowing or reticulating, a hydrophilic polyurethane described in United Kingdom Application No. 2093190. Suitable polyurethanes include the linear polyether polyurethanes described therein and which are incorporated herein by cross-reference. For use in the dressings of the present invention the hydrophilic polyurethanes are foamed using a conventional blowing agent or are reticulated by conventional means.

One way of forming the foam will be to cast a foamable composition onto a support to which it is not adherent and after curing the foam is recovered in the form of a sheet having a thickness of from 1 to 15 mm, more suitably 2 to 10 mm, preferably 3 to 5 mm. The sheet of foam may then be cut into pieces which have a size of 0.5×0.5 mm to 15×15 mm, and more suitably about 1×1 mm to 10×10 mm, preferably 3×3 to 7×7 mm and most preferably 3×3 to 5×5 mm.

The pieces used need not necessarily be uniformly shaped. Irregular shaped pieces would result from chopping the foam in, for example, a kitchen blender or a fixed blade comminutor. Pieces which have uniform shape such as parallelepiped or cuboid may be formed by cutting the cast foam sheet using scissors, a sharp knife or other sharp bladed mechanical device. It is preferred that the pieces are approximately cuboid in shape.

Alternatively the conformable hydrophilic polyurethane foam can be made by mixing together an isocyanate terminated polyether having functionality of more than two with a surfactant and water and casting the mixture onto a surface which is non-adherent to the foam. Preferred isocyanate terminated polyethers include Hypols FHP 2000, 20001, 3000, 3001, 2002 and 2000HD marketed by W. R. Grace & Co. Hypols are described in a booklet published by W. R. Grace & Co. "Hypol: foamable hydrophilic polymers-laboratory procedures and foam formulation". Their preparation and use are disclosed in British Patent Specifications No. 1,429,711 and 1,507,232.

Suitable surfactants for use in forming conformable hydrophilic polymer foams include non-ionic surfactants. Favoured non-ionic surfactants are oxyporpoylene-oxyethylene block copolymers known as Pluronics (trade mark) marketed by BASF Wyandotte. Preferred Pluronics include L64, F87, P38, P75 and L62. Another favoured non-ionic surfactant is a polyoxyethylene stearyl ether known as Brij 72 (trade mark) marketed by Honeywill Atlas.

To prepare a suitable foam, 100 parts by weight of Hypol 2000, 2001, 3000, 3001, 2002 or 2000HD is mixed with 0.3 to 7 parts by weight of surfactant or mixtures of surfactants and 30 to 300 parts by weight of water and the foaming mixture cast onto a surface. Typical foaming mixtures have a cream time of about 20 secs., a rise time of about 20 secs. and a cure time of about 400 secs.

A suitable mixing and dispensing machine is known as Vario-mix supplied by Frodef Engineering Limited. The foam mix can conventionally be delivered to the casting head by means of a 'fish tail' die.

Suitably the material which forms the porous bag will be flexible and elastic. As the hydrophilic foam contained within the bag may expand on absorbing wound exudate the material of the bag should be capable of extending to compensate for the increased volume of the contents of the bag and also should not tear under this increased strain. The material of the bag must be flexible so that it is conformable to the irregular contours of the wound cavity.

It is desirable that the material which forms the porous bag has a recoverable elastic strain of at least 20% and more suitable of at least 25%.

The material used to form the porous bag employed in the present invention is suitably an elastic, flexible material which has a soft feel when in contact with the skin and which is liquid permeable by virtue of apertures through it. By liquid permeable it is meant that the material has been adapted to allow the passage of liquids such as blood, water, and wound exudate. The material may possess apertures either by virtue of a manufacturing process, that is the material is an integral net or by forming the apertures in a film of the material by means of conventional methods including needling, electric discharge, vacuum perforation, hot jet perforation and moulding under heat and pressure on a suitable former or by fibrillation of an embossed film.

Aptly the material will be formed from a material having a reduced tendency to adhere to a moist wound surface. The material will be chosen to enclose the pieces of foam and to isolate the wound surface from contact with the foam. The material will not be adhered to the foam. The size of the apertures in the bag material will be chosen not only to prevent pieces of foam escaping from the bag but also to avoid corners of the pieces of foam protruding from the dressing and abrading the wound surface or adhering to it.

Aptly the polyurethane foam used may be a polyester or polyether polyurethane foam which may be formed from either a linear or cross-linked polyurethane. Suitably the foam will have a pore size of from 0.1 mm to 5 mm, and more suitably 0.2 to 4 mm and preferably 0.5 to 2.5 mm.

Aptly the foam used in the dressings of the present invention will be resilient. Suitably a 10 cm×10 cm cube of foam when subject to a pressure of 1 Kg/0.1 m$^2$ will collapse to less than 10% and preferably to less than 5% of its uncompressed hight and recover.

Suitably the ratio in size between an aperture and a dimension of a piece of foam is preferably at least 1:4 and is preferably 1:6 so that the aperture is significantly smaller than the size of a piece of foam so that there is little or no propensity for the pieces of foam to be shed from the dressings of the present invention.

Aptly the material used for forming the porous bag will be perforated polymeric film such as an integral net for example formed either by the fibrillation of embossed films of polymeric material by biaxially stretching the film or by casting the material from a solution onto an embossed former. Suitably the material is made from hydrophobic polymers including high or low density polyethylene, polypropylene, polyurethane, polystyrene or copolymers or mixtures thereof or styrene-butadiene or styrene-isoprene-block copolymers.

The apertures in the material may be any convenient shape but are favourably of a circular shape. Suitably the apertures will be 0.1 mm to 4 mm in diameter, more suitably 0.5 mm to 3 mm and preferably 1 to 2.5 mm in diameter. If the apertures are irregular then they will have an area equivalent to that of the circular apertures described above.

One favoured form of material for forming the porous bags for use in the present invention is as an integral net. Aptly such nets are formed by the fibrillation of a thermoplastic embossed polyolefin film comprising low and high density polyethylene, polypropylene or copolymers or blends thereof or blends of polyolefin with polystyrene. The manufacture of such a net is described in for example British Pat. Nos. 914489, 1055963, 1075487, 1106254, 1110051, 1261515, 1496786, 1531715, and 1548865, which patents are incorporated herein by cross-reference.

One preferred form of integral net may be formed by the process described in British Pat. No. 1548865. This net is formed from hydrophobic polymers which include high density polyethylene and a blend of a high density polyethylene and high impact polystyrene.

The structure of these nets is characterised in that they comprise substantially straight, parallel, smoooth longitudinal ribs connected by wholly or partly fibrillated strands. This structure gives the bag the strength and porosity required for a wound dressing as well as a particularly soft feel. Suitable nets formed by this process include those available as Net 909 (trade mark) Grades A4, A7 and H8C (available from Smith & Nephew Plastics Ltd., Gilberdyke, North Humberside).

A second favoured material for forming the porous bags for use in the present invention are integral cast nets such as those formed by the process described in our copending United Kingdom Application No. 2093702 at page 7 lines 20 to 38 which are incorporated herein by cross-reference. Suitably the net used in the wound dressings of the present invention are formed by casting a solution of a polyurethane.

A preferred material however for forming the porous bag used in the present invention is in the form of a contoured net. This net comprises a film which has a plurality of depressions impressed out of the plane of the film. Each of the depressions has an aperture at the bottom. The net therefore is not flat but has a finite thickness. The thickness is defined as the perpendicular distance between the aperture and the plane of the film. It has been found that these nets are flexible, elastic and have a particularly soft feel. The dressings of the invention are formed with the apertured depressions facing into the interior of the dressing, in this way the pieces of foam are maintained at a distance from the wound surface but without impending the absorption capacity of the dressing nor adversely affecting the rate at which wound exudate is taken into the dressing. The irregular packing of the pieces of foam within the dressing means that an aperture is not necessarily in contact with a piece of foam. This may be advantageous in allowing wound exudate better access to hitherto unused pieces of absorbent foam.

Suitable nets may be prepared by casting a solution of the material forming the net onto an embossed film and wiping the embossed film to make sure that the tops of the embossments are not covered by the casting solution. The solvent is then removed and the resulting net is carefully lifted from the embossed film. Suitable polymers for use in this solvent process include thermoplastic polyurethanes such as Estanes (trade mark, available from B. F. Goodrich) and styrene butadiene block copolymers such as the Cariflexes (trade mark).

Alternatively, the contoured net may be made as follows: a polymer film from which the net is to be prepared is placed on the embossed surface of a thermoplastic film. The embossments are suitably arranged in a pattern and are in the form of discrete, raised areas with troughs between them. The embossments may be any shape including square truncated pyramidal or hexagonal. A film of polyethylene is placed over the polymer film urging it against the embossments. The three layered sandwich is then subjected to pressure at elevated temperature, for example 80° C. for a period of time. The temperature, pressure and time required for the process will depend upon the properties of the polymer film but will be sufficient for the film to flow into the troughs between the embossments leaving the tops of the embossments uncovered. The pressure and heat are discontinued and the polyethylene film is removed. The contoured net material produced is peeled away from the embossed surface. The embossments may be pretreated with a release compound such as a silicone release compound to facilitate this separation. The net appears as a film having geometrically shaped depressions having approximately circular holes at the apex.

In a further alternative process the polymer film and embossed film may be first passed between a silicone-surfaced roller and a heated metal roller under pressure to ensure intimate contact between the film and the embossed film. The polyethylene film is placed over the polymer film as before and the three layer sandwich passed between two heated metal rollers to form the net.

Suitably the contoured net will have a thickness as hereinbefore defined of from 0.5 to 2 mm, more suitably 0.75 to 2 mm and preferably 1.0 to 1.5 mm. Suitably the apertures in the net will have an area equivalent to a circle of diameter 0.5 mm to 1.5 mm, and preferably 0.75 to 1.0 mm.

Polymeric material which is suitable for preparing contoured nets in the methods outlined above include thermoplastic elastomeric polymers or polymer blends. A favoured polymeric material is a blend of an ethylene-vinyl acetate copolymer and an incompatible polymer such as a polyolefin and particularly polystyrene. A particularly preferred polymeric material is a blend of from 40 to 90 parts by weight of ehtylene-vinyl acetate copolymer and 60 to 10 parts by weight of polystyrene and more preferably 60 to 90 parts ethylene-vinyl acetate copolymer and 40 to 10 parts polystyrene. If necessary the polymeric material may include fillers or whitening materials such as titanium dioxide.

The film from which the contoured net is formed may suitably have a thickness of from 50 $\mu$m to 120 $\mu$m and preferably 95 to 100 $\mu$m.

In a further aspect of the present invention a bulky non-woven fabric, usually called a fleece, may be present between the apertured film and the pieces of foam. The presence of this fleece makes the dressing softer, more resilient and more aesthetically pleasing and also acts to disperse the wound exudate as it passes through the apertured film bringing the exudate in contact with more absorbent more quickly. Suitable materials for forming the fleece include polyethylene, polypropylene, polyester, polyamide and the like. It is particularly desirable to employ a mixture of a minor proportion of a hydrophilic polymer in forming the fleece. A particularly apt mixture is 10% rayon/90% polyethylene. Suitably the fleece will have an uncompressed thickness of from 0.5 mm to 2 mm.

A second preferred material for forming the porous bags used in the present invention is a contoured net as described hereinbefore which has been coated on the embossed surface with polymer fibres formed by spraying a solution of the polymer whereby the solvent evaporates in flight and the fibres so formed are collected on the contoured net to form a non-woven fabric which is adhered to the contoured net. Observation of the coating using an optical microscope shows that some of the fibres bridge across the apertures but without deleteriously effecting the absorption of the dressing or without affecting the elasticity of the contoured net. Suitable polymers for forming a coating in this way are those which are soluble in volatile solvents and include polyurethanes and styrene-butadiene block copolymers.

The wound dressings of the present invention may further contain physiologically active components which are present in therapeutically effective amounts. The wound dressing may contain, for example, local anaesthetics, hormonal compounds, enzymes, antibacterial agents, antifungal agents, debriding agents and less favourably lubricating and barrier chemicals such as silicone compounds. The additional components will be compatible with the absorbent material used in the dressing. A preferred additional component is an antibacterial agent and is most preferably a water soluble antibacterial agent. Suitable antibacterial agents include chlorhexidine or a salt thereof, a silver salt such as sulver sulphadiazine or an acceptable iodine source such as povidone-iodine.

The physiologically active component may be incorporated into the foam during the process for manufacturing the foam or just prior to use by soaking in a solution of the components, the latter process is preferred for those physiologically active components which are particularly soluble in water. Thus for example a 5×5 cm dressing of this invention suspended in 100 ml of 5% w/v solution of chlorhexidine gluconate for 48 hr and dried was found to possess antibacterial properties.

The physiologically active component may be present by 0.2 to 20%, more usually from 0.3 to 10% and preferably 0.5 to 5% by weight of the dressing, for example 1%, 2% or 3%.

The wound dressing according to the invention may be placed in direct contact with the wound and held in place by conventional dressings such as a gauze bandage or other non-woven adhesive bandage. Mass transfer readily occurs through the porous, water and blood permeable bag to the pieces of foam inside the bag. The foam absorbs the exudate so that prevents blood or serum leaking out of the bag.

The wound dressing of this invention may be in any convenient form. One preferred form is a dressing of rectangular shape. The size of such dressings will depend upon the type of wound to which they are applied. Small pressure sores may require a dressing of width 1 to 5 cm and length 1 to 10 cm. Larger leg ulcers and burns may require dressings which are 10 cm to 20 cm×30 cm in a rectangular shape, or may require the use of more than one smaller pad. In a second preferred form the dressing may be in the form of an approximate circle or an oval. Suitably the diameter of a circular dressing may be from 1 to 30 cm.

A further form of the dressing is in the form of a long thin pouch or sausage shape in which the ratio of length to width may be 10:1 or greater. These dressings may be present as a single dressing or as a strip of several dressings from which individual dressings may be cut or a combination of 2 or more pouches may be used and packed into the wound cavity.

The amount of foam placed within its water permeable bag will, of course depend upon the size of the final dressing. The amount must be such as to absorb the expected amount of wound exudate and to pack the wound cavity. The amount of foam may be measured in terms of its dry uncompressed volume. Thus for example in a 6 cm×6 cm bag the dry volume of foam used to make a suitable dressing was 34 cc, in an octagonal dressing having a side of 2 cm the dry volume of foam required was 24 cc.

The thickness of the dressing will depend upon the amount of foam placed in the dressing. Suitably the dressing will be 0.5 to 3.0 cm in thickness, more suitably 1 to 2.5 cm and preferably 1.2 to 2.0 cm.

It is desirable that the wound dressings of this invention are sterile. The wound dressing of the invention is advantageously provided in bacteria impervious pouches. Such packed forms can be prepared under aseptic conditions or alternatively sterilised after packing by a conventional procedure. A favoured sterilisation procedure is by heat sterilisation. Alternatively the dressings may be sterilised by ethylene oxide or gamma irradiation. Most suitably the dressings are heat sealed in packages constructed of aluminium foil laminated with a heat sealable polymeric film such as polyethylene and sterilised in the package by irradiation.

In use, the sterile dressing of appropriate size is removed from its package and applied to the cavity of the wound to be treated and covered with a retaining dressing such as a conventional gauze bandage or, for sterile wounds, a moisture vapour permeable film dressing such as OpSite (trade mark).

In a further aspect the present invention provides a method of treating a deep and exuding wound by applying to the wound an absorbent non-adherent wound dressing comprising an absorbent material contained within a water permeable, porous bag characterised in that the absorbent material comprises individual pieces of a conformable resilient, absorbent, hydrophilic foam and the bag is formed from an apertured film.

The materials used in the absorbent dressings employed in deep and exuding wounds are those which have been described hereinbefore.

EXAMPLE 1

Preparation of a non-adherent absorbent wound dressing

Using a two component dispensing unit (Vario-mix supplied by Prodef Engineering Limited), a foaming mixture was formed by mixing Hypol FHP 2002 and Brij 72 (as a 2% aqueous solution) in the ratio of 1:2.25. The foaming mixture was fed into the coating head by means of an output nozzle in the form of a 15 cm 'fish tail' die and coated onto the casting surface by means of a knife over roller coating head set at a gap of 2 mm. The cast foam was dried by passage through an air circulating oven at a temperature of 50° C. for 5 minutes. The dried foam was then cut up into irregular shaped pieces which were approximately cuboid in shape and of side between 3 and 4 mm.

A piece of net material (Net 909 (trade mark) Grade H7, available from Smith & Nephew Plastics Ltd., Horncastle Trading Estate, Gilberdyke, North Humberside) was cut in the form of two octagons joined at one edge and having an edge of length 2 cm. The net was folded at its common side and five of the remaining edges heat sealed together so that a container was formed open on two sides. Pieces of the foam were placed inside the container and the remaining two sides sealed. Approximately 1 gm of foam provided a dressing of sufficient absorptive capacity, softness and thickness which was suitable for use on a cavernous exuding wound.

The dressing may be packaged in a bacteria proof pack and sterilised by means of gamma irradiation.

EXAMPLE 2

Individual pieces of a hydrophilic foam were prepared by a similar method to that described in Example 1.

A pattern of two octagons joined together along one edge was cut from a three dimensional fleece formed from 10% rayon and 90% polyethylene. The two octagons were folded together and carefully heat sealed along five of the remaining seven unsealed edges. Pieces of the hydrophilic foam were placed within the container of fleece so formed and the remaining two sides were heat sealed. The length of the side was 2 cm approximately.

Two octagons of the net material described in Example 1 were cut which were slightly larger than the nonwoven fleece container. The net material was placed on either side of the fleece containing the pieces of foam and heat sealed together at their edges. The resultant dressing had an absorptive capacity, softness and thickness which was suitable for use on cavernous exuding wounds.

EXAMPLE 3

Individual pieces of a hydrophilic foam were prepared by a similar method to that described in Example 1.

A film of thermoplastic polymer comprising a blend of ethylvinyl acetate (60 parts) and a high impact polystyrene (40 parts) was placed on the embossed surface of a plastics sheet which had a pattern of raised, discrete, hexagonal bosses on one surface. A film of polyethylene was placed so that the thermoplastic sheet was sandwiched between the embossed sheet and the flat polyethylene sheet. This sandwich was subjected to pressure and heat, 80° C. for 5 minutes, and the polyethylene sheet removed. The thermoplastic polymer had been formed into a contoured net material under the influence of the heat and pressure and could be peeled away from the embossed surface of the thermoplastic polymer. Two pieces of contoured net were cut having dimensions of 6 cm×6 cm and heat sealed along three sides. Pieces of the hydrophilic foam 1.5 g), 34 cc dry uncompressed volume, were packed into the pouch formed from the net and the final side heat sealed. The square dressing so formed was suitable for use on a cavernous exuding wound.

EXAMPLE 4

A wound dressing was formed in a similar manner to that described in Example 2 except that the net material used was a contoured net formed by the process described in Example 3.

EXAMPLE 5

Individual pieces of a hydrophilic foam were prepared by a similar method to that described in Example 1.

A film of thermoplastic polymer was formed by extruding a blend of ethylene-vinyl acetate copolymer, 90 parts by weight high impact polystyrene, 10 parts by weight and titanium dioxide, 4% weight of weight of the polymers. The film had a thickness of 75 $\mu$m. A strip of the film was placed on an embossed film of polyethylene having hexagonal embossments arranged so that there were 10 embossments per sq. cm (approximately). The two films were passed in contact between the nip of two rollers under pressure, a silicone rubber coated roller and a metal roller heated to 100° C. Then a rigid plain film of polyethylene was then placed on top of the polymer blend film and a second pass was made between the nip of two metal rollers heated to 100° C. The film sandwich was allowed to cool, the polyethylene film removed and the net carefully peeled from the embossed film. The apertures formed by this process were roughly circular in shape and had a diameter of 0.8 mm (approximately).

Two pieces of the net were cut having dimensions such that a circle 3 cm in diameter could be formed from the pieces. A first circular radio frequence welder was used to form a pouch. Pieces of the hydrophilic foam were placed into the pouch, about 0.4 g were placed in a pouch of this size and the pouch was sealed using a second welder and the sealed pouch trimmed to give a dressing which was 3 cm in diameter.

The resultant dressing had an absorptive capacity, softness and thickness suitable for use as a dressing for cavernous exuding wounds.

The dressing may be sterilised using either ethylene oxide or gamma irradiation and packed in a bacteria proof package until ready for use.

In a dressing employing a polymer blend of the composition given above, a dressing of 2.5 cm diameter used 0.4 g (dry weight) of hydrophilic foam pieces, a dressing of 5 cm diameter uses 3.5 g (dry weight) of hydrophilic foam pieces and a dressing of 10 cm diameter uses 25 g (dry weight) of hydrophilic foam pieces.

EXAMPLE 6

Individual pieces of a hydrophilic foam were prepared by a similar method to that described in Example 1.

A contoured net was formed in a similar manner to that described in Example 5.

A solution of a styrene-butadiene block copolymer was formed in dichloromethane. This solution was sprayed onto the embossed side of the contoured net from such a distance that in flight the solvent evaporated and the block copolymer was collected on the embossments as a random array of fibres which adhered to the net. Observation of the final coated net using an optical microscope showed that fibres of the block copolymer criss-crossed the apertures in the film without blocking them.

This material was used to form pouches which were filled with the hydrophilic foam and may be sterilised using gamma irradiation.

Demonstration of Effectiveness

A block of polymethyl methacrylate (Perspex, trade mark) was cast with an irregular shaped cavity formed about the centre of one face. The cavity had a depth of about 1.5 cm and had a volume of 23 cc. The floor of the cavity was rounded where it met the walls of the cavity so as to simulate a cavernous wound. A hole was drilled through the bottom of the cavity and through the block. In the test a thin tube was placed through the hole so that fluid could be delivered to the floor of the cavity via the tube. The tube was adapted to deliver horse serum via a peristaltic pump which had been programmed to delivery 6 ml of horse serum in a 24 hour period, the most rapid delivery rate being at the beginning of the period and the slowest rate towards the end. This simulated the generation of wound exudate by an exuding wound. In the test the surface of the cavity was wetted and hte dressing packed into the cavity and covered with a moisture vapour permeable polyurethane film (OpSite) for 24 hours. 6 ml of horse serum were delivered to the cavity during this period.

After 24 hours the cover was removed from the dressing and the dressing removed. The dressing was assessed to see if it had conformed to the shape of the cavity and if it had absorbed the serum from the cavity. The wound dressings prepared and constructed in the manner described in Examples 1 to 4 showed that they were both conformable and had sufficient absorption capacity to be suitable for use on cavernous, exuding wounds.

A dressing having a square shape 6 cm×6 cm, with a net cover of Net 909 Grade H7 and filled with Hypol FHP 2002 foam piece, dry volume 34 cc was particularly suitable for the artificial cavity.

I claim:

1. A sterile, absorbent, non-adherent wound dressing suitable for use on deep wounds which dressing comprises an absorbent material contained within a porous bag, said absorbent material comprising individual pieces of a conformable, resilient, absorbent hydrophilic foam and said bag being formed from a perforated polymeric film and in which there is additionally present between the perforated polymeric film and the pieces of foam a non-woven fabric comprising a mixture of rayon and polypropylene fibers with an uncompressed thickness of from 0.4 to 2 mm.

2. A wound dressing according to claim 1 in which the hydrophilic foam is an open cell foam in which the cell size is from 30 μm to 700 μm and from 20 to 70% of the total membrane area of the cells are membrane openings.

3. A wound dressing according to claim 1 in which the pieces of foam have dimensions of from 3×3 to 7×7 mm and have a thickness of from 2 to 10 mm.

4. A wound dressing according to claim 1 in which the hydrophilic foam is a hydrophilic polyurethane foam.

5. A wound dressing according to claim 1 in which the hydrophilic foam is a foam containing a non-ionic surfactant.

6. A sterile, absorbent, non-adherent wound dressing suitable for use on deep wounds which dressing comprises an absorbent material contained within a porous bag, said absorbent material comprising individual pieces of a comfortable, resilient, absorbent hydrophilic foam and said bag being formed from a perforated polymeric film, in which the perforated film is in the form of a contoured net comprising a film of thermoplastic elastomer having depressions impressed out of the plane of the film each depression having an aperture at the bottom.

7. A wound dressing according to claim 6 in which the thermoplastic elastomer comprises a blend of 40 to 90 parts by weight ethylene-vinyl acetate copolymer and 60 to 10 parts by weight of polystyrene.

8. A wound dressing according to claim 6 in which the area of an aperture is equivalent to the area of a circle having a diameter of 0.5 to 3 mm.

9. A wound dressing according to claim 6 in which the contoured net has fibers adhered to the depressions impressed out of the plane of the film whereby the apertures are crossed by the fibers.

10. A wound dressing according to claim 9 in which the fibres are formed by spraying a solution of the polymer of the fibres in a volatile solvent allowing the solvent to evaporate and catching the fibres so formed in the embossed surface of the contoured net.

11. A wound dressing according to claim 1 or 6 in which the dressing additionally contains a therapeutically effective amount of a physiologically active agent.

12. A wound dressing according to claim 1 or 6 which is sterile and is packaged in a bacteria proof pack.

13. A wound dressing according to claim 6 in which the hydrophilic foam is an open cell foam in which the cell size is from 30 μm to 70 μm and from 20 to 70% of the total membrane area of the cells are membrane openings.

14. A wound dressing according to claim 6 in which the pieces of foam have dimensions of from 3×3 mm to 7×7 mm and have a thickness of from 20 to 10 mm.

15. A wound dressing according to claim 6 in which the hydrophilic foam is a hydrophilic polyurethane foam.

16. A wound dressing according to claim 6 in which the hydrophilic foam is a foam containing a non-ionic surfactant.

17. A method of treating a deep and exuding wound by applying to the wound a sterile absorbent, non-adherent wound dressing comprising an absorbent material contained within a water permeable porous bag, said absorbent material comprising individual pieces of conformable, resilient, absorbent hydrophilic foam and said bag being formed from a perforated polymeric film and in which there is additionally present between the perforated polymeric film and the pieces of foam a non-woven fabric comprising a mixture of rayon and polypropylene fibers with an uncompressed thickness of from 0.4 to 2 mm.

18. A method of treating a wound according to claim 17 in which the hydrophilic foam is an open cell foam in which the cell size is from 30 μm to 700 μm and from 20 to 70% of the total membrane area of the cells are membrane openings.

19. A method according to claim 17 in which the pieces of foam have dimensions of from 3×3 to 7×7 mm and have a thickness of from 2 to 10 mm.

20. A method according to claim 17 in which the hydrophilic foam is a hydrophilic polyurethane foam.

21. A method according to claim 17 in which the hydrophilic foam is a foam containing a non-ionic surfactant.

22. A method of treating a deep and exuding wound by applying to the wound a sterile absorbent, non-adherent wound dressing comprising an absorbent material contained within a water permeable porous bag, said absorbent material comprising individual pieces of a conformable, resilient, absorbent hydrophilic foam and said bag being formed from a perforated polymeric film, in which the perforated polymeric film is in the form of a contoured net comprising a film of thermoplastic elastomer having depressions impressed out of the plane of the film each depression having an aperture at the bottom.

23. A method according to claim 22 in which the thermoplastic elastomer comprises a blend of 40 to 90 parts by weight ethylene-vinyl acetate copolymer and 60 to 10 parts by weight of polystyrene.

24. A method according to claim 22 in which the area of an aperture is equivalent to the area of a circle having a diameter of 0.5 to 3 mm.

25. A method according to claim 22 in which the contoured net has fibers adhered to the depressions impressed out of the plane of the film whereby the apertures are crossed by the fibers.

26. A method according to claim 25 in which the fibers are formed by spraying a solution of the polymer of the fibers in a volatile solvent allowing the solvent to evaporate and catching the fibers so formed in the embossed surface of the contoured net.

27. A method according to claim 22 in which the dressing additionally contains a therapeutically effective amount of a physiologically active agent.

* * * * *